US00PP23118P2

(12) United States Plant Patent
Scheys

(10) Patent No.: US PP23,118 P2
(45) Date of Patent: Oct. 16, 2012

(54) ***HEUCHERA* PLANT NAMED 'BINOCHE'**

(50) Latin Name: ***Heuchera* hybrid**
Varietal Denomination: Binoche

(76) Inventor: Diederik A. M. Scheys, Pellenberg (BE)

( * ) Notice: Subject to any disclaimer, the term of this patent is extended or adjusted under 35 U.S.C. 154(b) by 89 days.

(21) Appl. No.: 12/931,606

(22) Filed: Feb. 4, 2011

(51) Int. Cl.
*A01H 5/00* (2006.01)

(52) U.S. Cl. ..... Plt./440

(58) Field of Classification Search ..... Plt./440
See application file for complete search history.

*Primary Examiner* — June Hwu
(74) *Attorney, Agent, or Firm* — Penny J. Aguirre

(57) ABSTRACT

A new cultivar of hybrid *Heuchera* named 'Binoche', characterized by its foliage with leaves that are very dark black-green, with the color consistent throughout the leaf, its leaves with ruffled margins that are cupped at the base, its leaves that have a glossy surface when young and becoming pubescent when mature, its ruffled leaf margins, its vigorous growth habit in comparison to other dark foliaged cultivars of *Heuchera*, and its cold hardiness in at least U.S.D.A Zone 4.

2 Drawing Sheets

Botanical classification: *Heuchera* hybrid.
Cultivar designation: 'Binoche'.

BACKGROUND OF THE INVENTION

The present invention relates to a new and distinct cultivar of *Heuchera* of hybrid origin, botanically known as a *Heuchera* and is hereinafter referred to by its cultivar name 'Binoche'.

The inventor selected the new cultivar, 'Binoche' as a single unique plant that arose from a controlled cross made in summer of 2007 in his nursery in Pellenberg, Belgium between the female parent 'Frosted Violet' (U.S. Plant Pat. No. 15,085) and the male parent 'Blackout' (U.S. Plant Pat. No. 20,613).

Asexual reproduction of the new cultivar was first accomplished under direction of the inventor by in vitro propagation in Rijswijk, The Netherlands in January of 2008. Asexual reproduction of the new cultivar has shown that the unique features are stable and reproduced true to type in successive generations.

SUMMARY OF THE INVENTION

The following traits have been repeatedly observed and represent the characteristics of the new cultivar. These attributes in combination distinguish 'Binoche' as a new and unique cultivar of *Heuchera*.

1. 'Binoche' exhibits unique foliage with leaves that are very dark black-green, with the color consistent throughout the leaf (monochromatic).
2. 'Binoche' exhibits leaves that have a glossy surface when young and becoming pubescent when mature.
3. 'Binoche' exhibits leaves with a lightly ruffled edge.
4. 'Binoche' exhibits leaves that are cupped near the petiole.
5. 'Binoche' exhibits a vigorous growth habit in comparison to other dark foliaged cultivars of *Heuchera*.
6. 'Binoche' is cold hardy at least in U.S.D.A. Zone 4.

'Binoche' can be most closely compared to its parent plants. 'Frosted Velvet', the female parent, differs from 'Binoche' in having foliage that had less ruffled edges, less cupped near the petiole, is less dark in color and exhibits a distinct silvery overlay that is lacking for the foliage of 'Binoche'. 'Blackout', the male parent, differs from 'Binoche' in having foliage that are shiny as mature leaves and lack any pubescence, and in having shorter and less erect flower stems.

'Binoche' can be compared to 'Obsidian' (U.S. Plant Pat. No. 14,836) and 'Black Beauty' (U.S. Plant Pat. No. 13,288) for its similarity in leaf color. In comparison to 'Obsidian', 'Binoche' has a more vigorous growth habit and leaves that is darker under various light conditions, darker when they emerge and glossier. In comparison to 'Black Beauty', 'Binoche' has leaves that are darker and less red in color.

BRIEF DESCRIPTION OF THE DRAWING

The accompanying colored photographs illustrate the overall appearance and distinct characteristics of the new *Heuchera*. The photographs were taken of a plant two years in age as grown outdoors in a 1.5-liter container.

The photograph in FIG. 1 provides a side view of the plant habit and typical mid summer coloration of the foliage of 'Binoche'.

Figure 2:
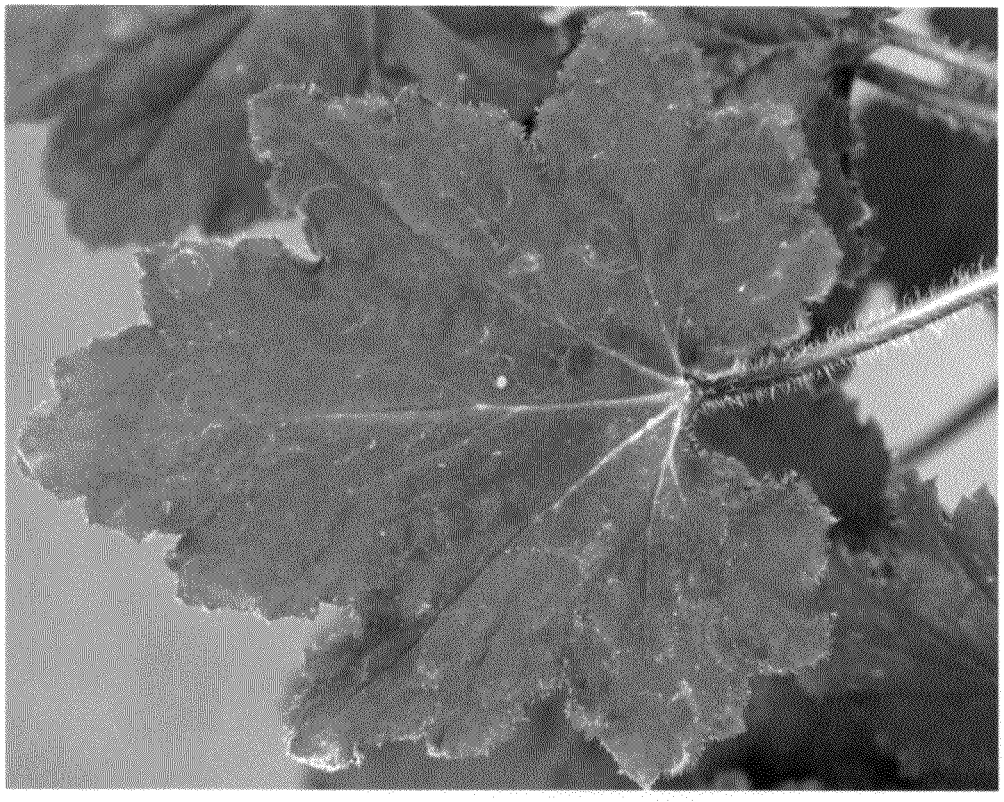

The photograph in FIG. 2 provides a close-up view of the foliage of 'Binoche'.

Figure 1:
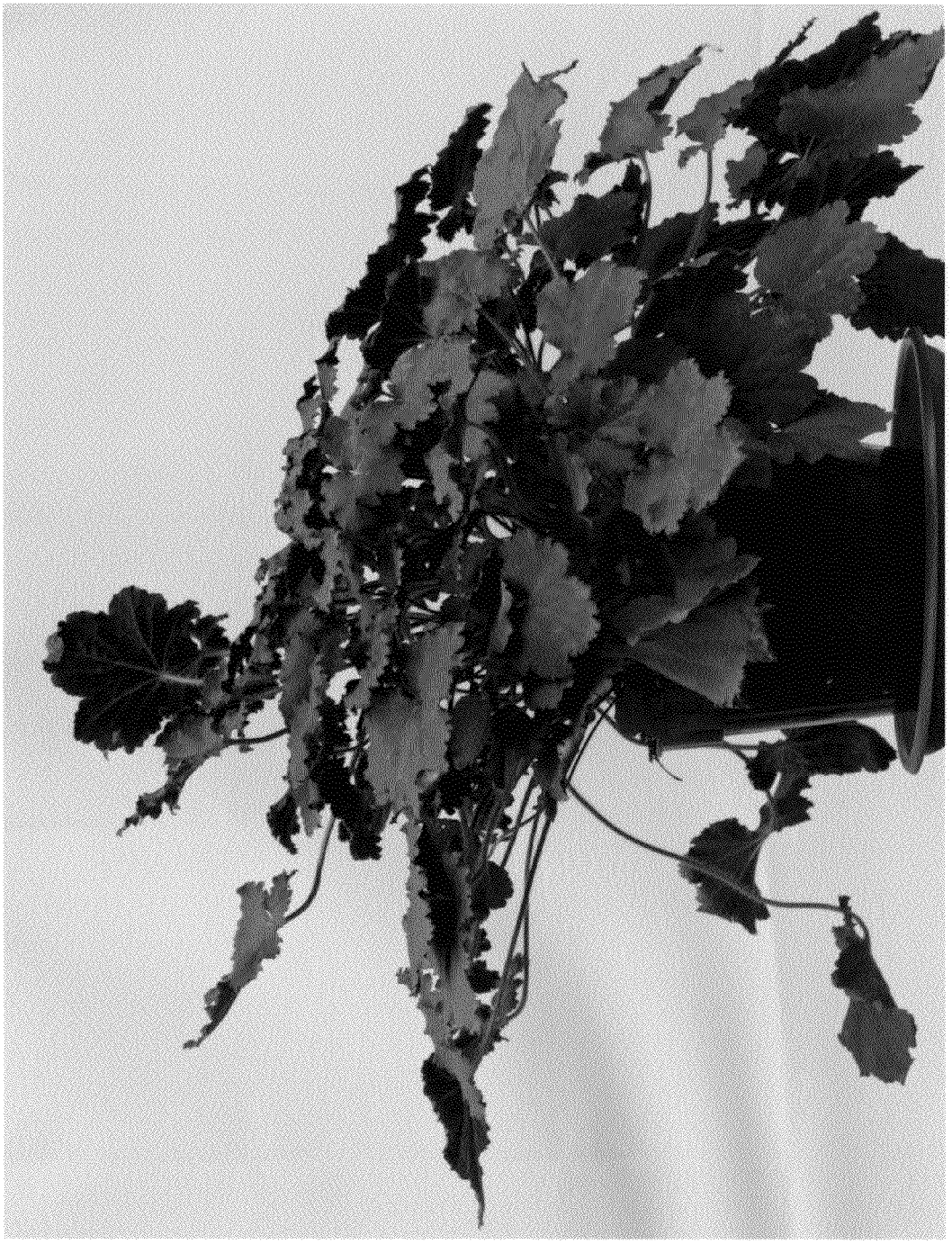
Figure 3:
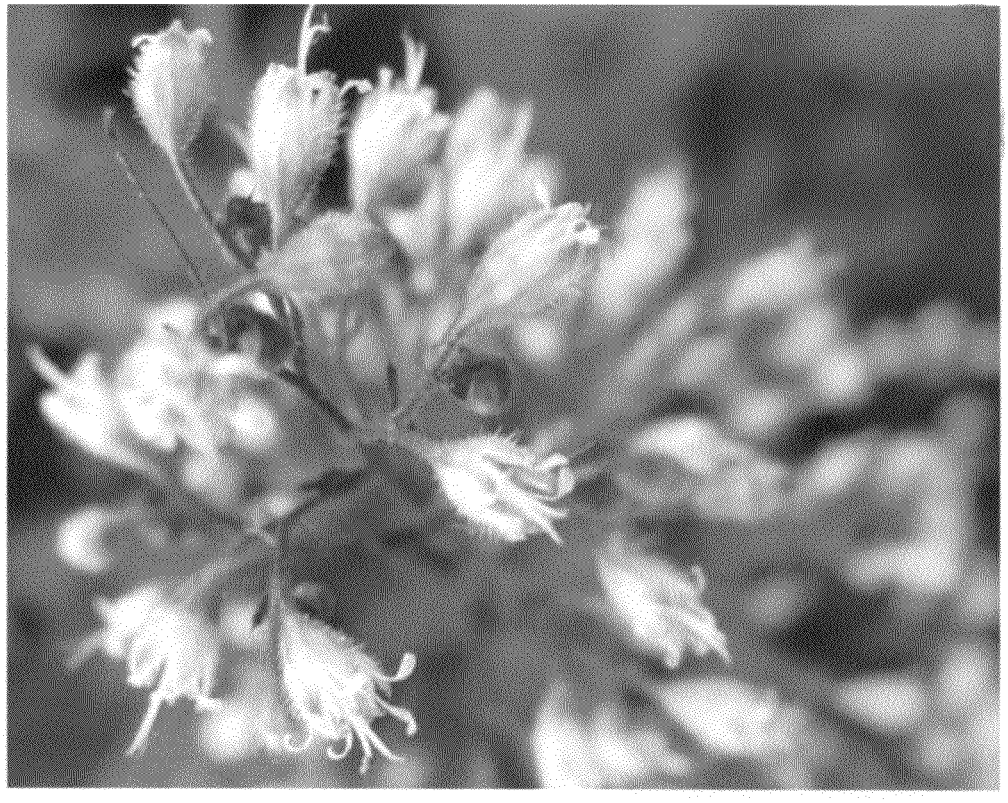

The photograph in FIG. 3 provides a close-up view of the flowers of 'Binoche'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 2-year-old plants of the new cultivar as grown outdoors in 1.5-liter containers in The Netherlands. Plants were grown under average day temperatures of 10° to 20° C. and average night temperatures of 2° to 12° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant habit*.—Compact, clump-forming herbaceous perennial, mounded foliage.

*Height and spread*.—Reaches a height of 26.5 cm in height and about 49.4 cm in width when mature.

*Cold hardiness*.—At least to U.S.D.A. Zone 4.

*Diseases and pests*.—Disease free in the conditions tested, no susceptibility or resistance to pests has been observed.

*Root description*.—Fibrous roots on woody rootstalks.

*Branching habit*.—Basal rosettes of leaves on petioles.

*Basal branching*.—Rosettes and short stems grow from the base.

*Propagation*.—In vitro propagation is the preferred method, division are also possible.

*Growth rate*.—Vigorous for a dark foliaged *Heuchera*.

Stem description:

*Shape*.—Rounded.

*Stem color*.—N200A, with leaf scars a color between 156A and 199D.

*Stem size*.—An average of 0.8 cm in diameter and 1.5 cm in height.

*Stem strength*.—Very strong.

*Stem aspect*.—Rounded.

*Stem surface*.—Rugose and dull, consisting of leaf-scars.

*Stem number*.—Average of 7.

*Internode length*.—Average of 0.1 cm in length.

*Branching*.—Main stem with an average of 7 rosettes.

Foliage description:

*Leaf shape*.—Broadly ovate.

*Leaf division*.—Simple.

*Leaf base*.—Hastate, touching but not overlapping, cupped.

*Leaf apex*.—Acute.

*Leaf venation*.—Laciniate.

*Leaf margins*.—Lobed with average of 9 lobes per leaf, lobe margins crenate, slightly ruffled.

*Leaf attachment*.—Petiolate.

*Leaf arrangement*.—Basal rosettes.

*Leaf orientation*.—Typically nearly horizontal to petiole.

*Leaf surface*.—Young leaves upper and lower surface; shiny, mature leaves upper surface; dull and slightly pubescent, lower side is moderately glossy with pubescent on main and secondary veins with a sparse covering of short white hairs 1.5 mm in length and 156D in color.

*Leaf color*.—Young upper surface; N199B to N199A, young lower surface; 186C to 200A, mature upper surface; between 147A and N189A, mature lower surface; N187A.

*Leaf size*.—Average of 9.1 cm in length and 8.8 cm in width.

*Leaf quantity*.—18 per basal rosette.

*Vein color*.—Upper side; between 147B to 147C, lower surface; 197A.

*Petioles*.—Round in shape, average of 21.8 cm in length and 2.8 mm in width, color; 200C and 197A towards apical portion and N186C towards the base, surface is densely covered in short hairs an average of 2 mm in length and 156D in color.

*Stipules*.—Leafy stipules at the base of each leaf with an average of 1 cm in length and 4 mm in width and N77A to N77B in color.

Flower description:

*Inflorescence type*.—Numerous small bell-shaped flowers arranged on pyramidal panicles on flower scapes emerging from the base of the rosette, each peduncle has 2 pairs of lateral flowers and a terminal flower.

*Inflorescence size*.—An average of 45 cm in height (including peduncle) and about 8 cm in width in full bloom.

*Inflorescence number*.—An average of 5 per 2-liter container.

*Flower fragrance*.—None detected.

*Flower quantity*.—Average of 200 flowers per flowering stem.

*Flower lastingness*.—Average of 4 days per flower, individual panicles blooms for about 3 weeks, flowers persistent.

*Flower buds*.—Broadly elliptic in shape, an average of 1.5 mm in diameter and 2.5 mm in depth, 60D in color.

*Flower aspect*.—Drooping to slightly outward on peduncles held nearly horizontal to rachis.

*Flower type*.—Campanulate.

*Flower size*.—About 2.5 mm in diameter and 5 mm in depth.

*Petals*.—About 5, rotate arrangement and implanted in hypanthium at base, narrowly elliptic in shape, margin is entire, apex is narrowly apiculate, upper and lower surface is glabrous and dull, color of upper and lower surface when opening and mature is N155B and suffused with 65B, about 2.5 mm in length and 0.5 mm in width.

*Calyx*.—Campanulate, sepals fused to hypanthium, 2.5 mm in depth and 2 mm in diameter.

*Sepals*.—5, un-fused portion is elliptic in shape, about 2.5 mm in length and 0.6 mm in width, margin is entire, apex is acute, base is fused, surface is densely covered with very short glandular hairs about 65D in color, color of upper and lower surface 60D.

*Bracts*.—1, at base of peduncle, lanceolate in shape, 60D in color, about 8 mm in length and 1 mm in width, acute, base truncate.

*Peduncles*.—Average of 4 cm in length and an average of 0.8 mm in width, held from a 45° angle to horizontal to rachis, color 182C, surface pubescent.

*Pedicels*.—Average of 2 mm in length and 0.3 mm in width, color 182C, puberulent surface, terminal is straight from peduncle and laterals are held at about a 45° angle.

*Rachis (flower scape)*.—Average of 40 cm in length and an average of 3 mm in width, 182A in color, surface is slightly puberulent, peduncle internode length is an average of 1.5 cm.

Reproductive organs:

*Gynoecium*.—2 Pistils, club-shaped, about 4 mm in length, stigmas minute and N155B in color, styles are about 4 mm in length and about N155B in color, ovaries are superior and 144C in color.

*Androcoecium*.—About 5 stamens, anthers are ovate in shape, basifixed, about 0.4 mm pollen was not observed.

*Seed*.—Seed development has not been observed.

It is claimed:

1. A new and distinct cultivar of hybrid *Heuchera* plant named 'Binoche' as herein illustrated and described.

* * * * *